United States Patent
Feloney

(10) Patent No.: US 8,202,263 B2
(45) Date of Patent: Jun. 19, 2012

(54) VAGINAL BARRIER AND FEMALE URETHRAL CATHETERIZATION ASSISTING DEVICE

(76) Inventor: Michael Feloney, Omaha, NE (US)

( * ) Notice: Subject to any disclaimer, the term of this patent is extended or adjusted under 35 U.S.C. 154(b) by 552 days.

(21) Appl. No.: 12/378,266

(22) Filed: Feb. 11, 2009

(65) Prior Publication Data

US 2010/0204666 A1    Aug. 12, 2010

(51) Int. Cl.
*A61F 5/455* (2006.01)

(52) U.S. Cl. ........ 604/330; 604/329; 604/347; 604/544; 600/574

(58) Field of Classification Search .......... 604/329–331, 604/347, 544; 600/574
See application file for complete search history.

(56) References Cited

U.S. PATENT DOCUMENTS

| | | | |
|---|---|---|---|
| 3,116,734 A * | 1/1964 | Terman | 604/329 |
| 3,347,238 A * | 10/1967 | Gresham | 604/329 |
| 3,351,050 A * | 11/1967 | Naftolin | 600/574 |
| 3,528,423 A * | 9/1970 | Lee | 604/329 |
| 3,583,388 A * | 6/1971 | Hovick | 600/574 |
| 3,683,914 A * | 8/1972 | Crowley | 604/329 |
| 3,776,235 A * | 12/1973 | Ratcliffe et al. | 604/329 |
| 3,815,581 A * | 6/1974 | Levin | 600/574 |
| 4,023,560 A * | 5/1977 | Cade et al. | 600/574 |
| 4,139,006 A * | 2/1979 | Corey | 600/29 |
| 4,194,508 A * | 3/1980 | Anderson | 604/329 |
| 4,198,979 A * | 4/1980 | Cooney et al. | 604/329 |
| 4,233,978 A * | 11/1980 | Hickey | 604/347 |
| 4,246,901 A * | 1/1981 | Frosch et al. | 604/329 |
| 4,563,183 A * | 1/1986 | Barrodale et al. | 604/329 |
| 4,615,692 A * | 10/1986 | Giacalone et al. | 604/94.01 |
| 4,815,151 A * | 3/1989 | Ball | 4/144.3 |
| 4,846,817 A * | 7/1989 | Mohr et al. | 604/329 |
| 4,875,898 A * | 10/1989 | Eakin | 604/331 |
| 5,045,078 A * | 9/1991 | Asta | 604/329 |
| 5,084,036 A * | 1/1992 | Rosenbaum | 604/329 |
| 6,238,383 B1 * | 5/2001 | Karram et al. | 604/544 |
| 6,428,521 B1 * | 8/2002 | Droll | 604/329 |
| 6,544,240 B1 * | 4/2003 | Borodulin et al. | 604/329 |
| 7,104,980 B1 * | 9/2006 | Laherty et al. | 604/528 |
| 2006/0100607 A1 * | 5/2006 | Brown | 604/544 |
| 2007/0197983 A1 * | 8/2007 | Giles Finn | 604/347 |
| 2010/0256580 A1 * | 10/2010 | Faber | 604/329 |

OTHER PUBLICATIONS

Recess definition, Webster's Third New International Dictionary, Unabridged, 1993, Merriam-Webster, Inc.*
Recess definition, The American Heritage dictionary of the English Language, 2007, Houghton Mifflin Co.*
Cleft definition, Webster's Third New International Dictionary, Unabridged, 1993, Merriam-Webster, Inc.*

* cited by examiner

*Primary Examiner* — Melanie Hand
*Assistant Examiner* — Paula Craig
(74) *Attorney, Agent, or Firm* — Suiter Swantz pc llo

(57) ABSTRACT

The vaginal barrier and female urethral catheterization assisting device system may include a semi-rigid member that is configured for positioning within a vagina. The system may include a generally longitudinal base member that is affixed to the semi-rigid member. The generally longitudinal base member may define a recessed portion distal to the semi-rigid member. The recessed portion may be configured to allow a catheter to be inserted into a urethra.

9 Claims, 5 Drawing Sheets

VAGINAL BARRIER AND FEMALE URETHRAL CATHETERIZATION ASSISTING DEVICE

TECHNICAL FIELD

The present disclosure generally relates to the field of personal medical devices, and more particularly to a device that may assist in inserting a catheter into a patient's urethra.

BACKGROUND

A patient or medically trained personnel may need to insert a catheter into the patient's urethra to assist the patient with excretion of bodily waste. However, the catheter may be inserted into the patient's vaginal opening by mistake, which may lead to a contaminated catheter. If the catheter is then taken out and inserted into the urethra, contaminants may be introduced into the urethra. The introduction of contaminants may lead to a urinary tract or nosocomial infection.

Furthermore, inserting the catheter may require the patient or medically trained personnel inserting the catheter to separate the patient's labia, and while keeping the patient's labia separated, inserting the catheter into the patient's urethra.

SUMMARY

The vaginal barrier and female urethral catheterization assisting device system may include a semi-rigid member that is configured for positioning within a vagina. The system may include a generally longitudinal base member that is affixed to the semi-rigid member. The generally longitudinal base member may define a recessed portion distal to the semi-rigid member. The recessed portion may be configured to allow a catheter to be inserted into a urethra.

The vaginal barrier and female urethral catheterization assisting device system may include a semi-rigid member that is configured for positioning within a vagina. The system may include a generally longitudinal base member. The generally longitudinal base member may define a recessed portion distal to the semi-rigid member. The system may also include a connector member. The connector member may be disposed between the semi-rigid member and the generally longitudinal base member. The recessed portion may be configured to allow a catheter to be inserted into a urethra.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

Referring to FIGS. 1-4, diagrams illustrating embodiments of a system 100 is shown. The system 100 may include a semi-rigid member 102 that is configured for positioning within a patient's vagina. The system 100 may include a generally longitudinal base member 104 that is affixed to the semi-rigid member 102. The generally longitudinal base member 104 may define a recessed portion 106 distal to the semi-rigid member 102. The recessed portion 106 may be configured to allow a catheter to be inserted into a urethra of the patient.

It is contemplated that users of the present disclosure may include an urologist, physician support staff, and like trained personnel when catheterizing a patient. Furthermore, a patient may utilize the present disclosure to self-catheterize herself.

The generally longitudinal base member 104 may be configured to keep the labia minora separated while the system 100 is properly inserted in the patient's vagina. By keeping the labia minora separated, the system 100 may allow a patient to self-catheterize herself using one hand.

The semi-rigid member 102 and the generally longitudinal base member 104 may be manufactured of silicone and/or a plastic deposit. For instance, the plastic deposit may be comprised of a polymer suitable for intra-bodily exposure, including surgical grade materials, and the like.

System 100 may reduce the likelihood of a patient contracting a urinary-tract and nosocomial like infections when being catheterized, such as when performed by medical staff or personally. When the semi-rigid member 102 is properly positioned in the patient's vagina, the system 100 may prevent the insertion of a catheter into the patient's vagina by mistake. Rather, the recessed portion 106 may be configured to allow insertion of the catheter into the patient's urethra. Furthermore, the recessed portion 106 may act as a guide for the catheter to the patient's urethra.

An alternative embodiment of system 100 may include configuring the generally longitudinal base member 104 to further cover a patient's anus, which may prevent a mistaken insertion of a catheter into the patient's rectum.

The present disclosure may help maintain a sterile catheter by preventing a catheter from mistakenly entering the patient's vagina or rectum. Additionally, the system 100 may temporarily reduce vaginal prolapse when properly positioned in a patient's vagina. The reduction of vaginal prolapse may expose a patient's urethra meatus, which may allow insertion of a catheter into the patient's urethra.

Figures 1A, 1B:
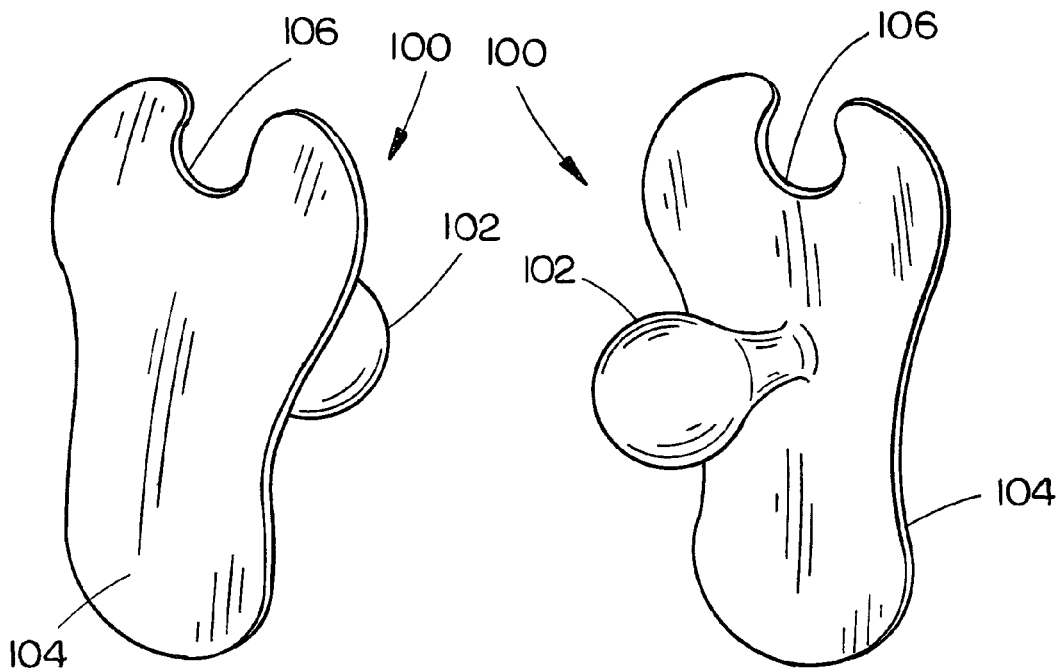
FIGS. 1A and 1B are isometric views of the vaginal barrier and female urethral catheterization assisting device system.
Figures 1C, 1D:
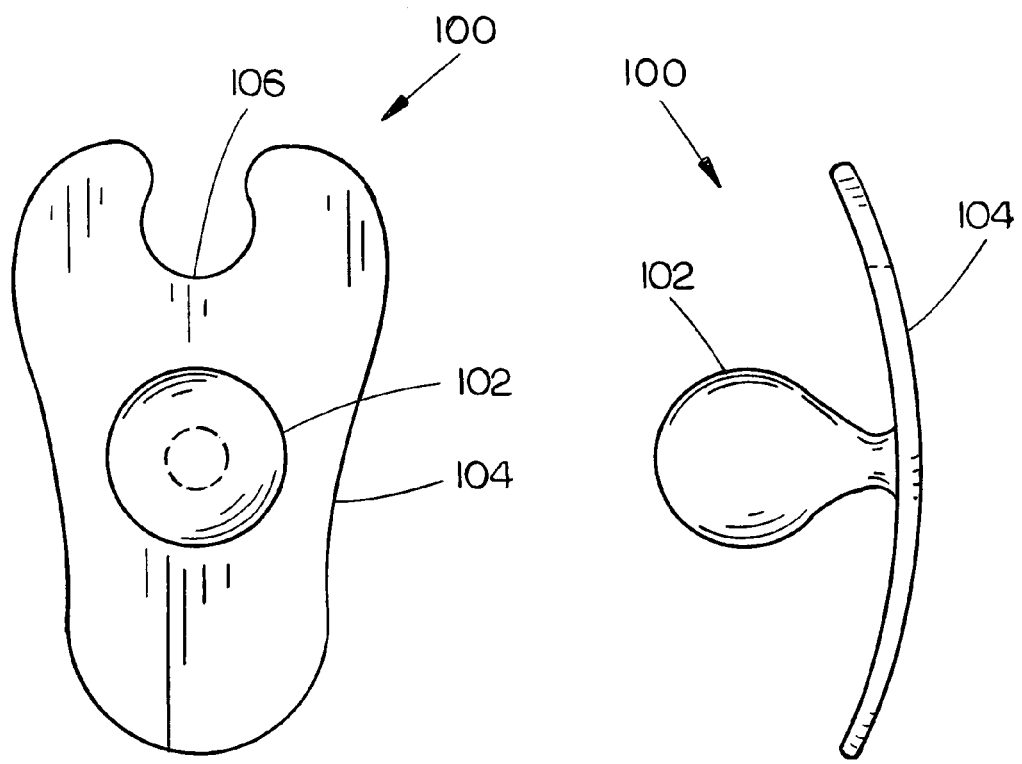
FIG. 1C is a top plan view of the vaginal barrier and female urethral catheterization assisting device system.
FIG. 1D is a side-view of the vaginal barrier and female urethral catheterization assisting device system.
Figures 2A, 2B:
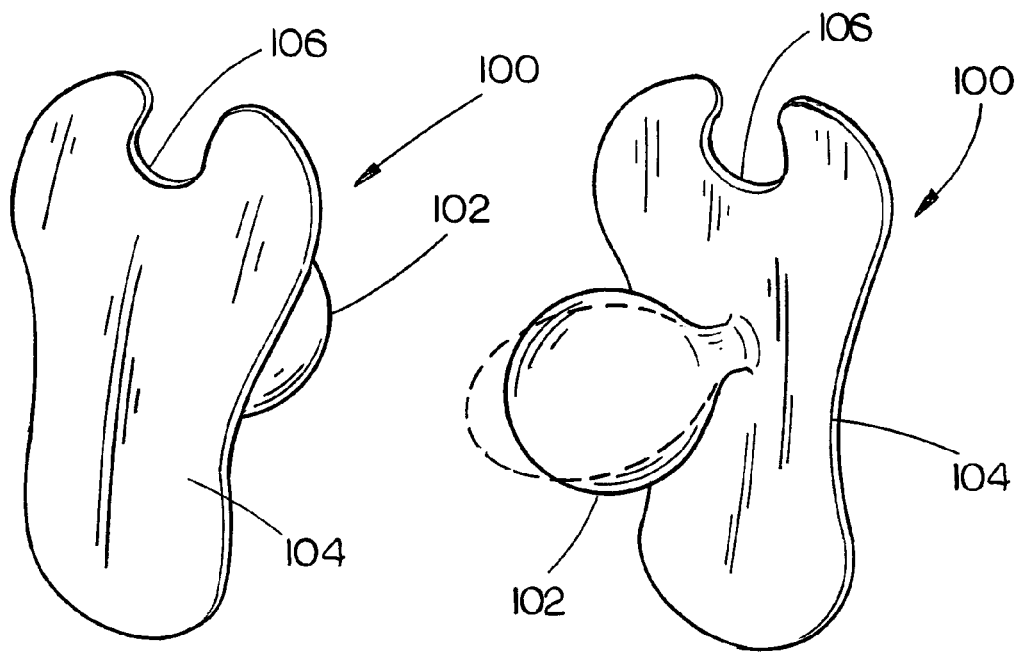
FIGS. 2A and 2B are isometric views of an alternative embodiment of the vaginal barrier and female urethral catheterization assisting device system.
Figures 2C, 2D:
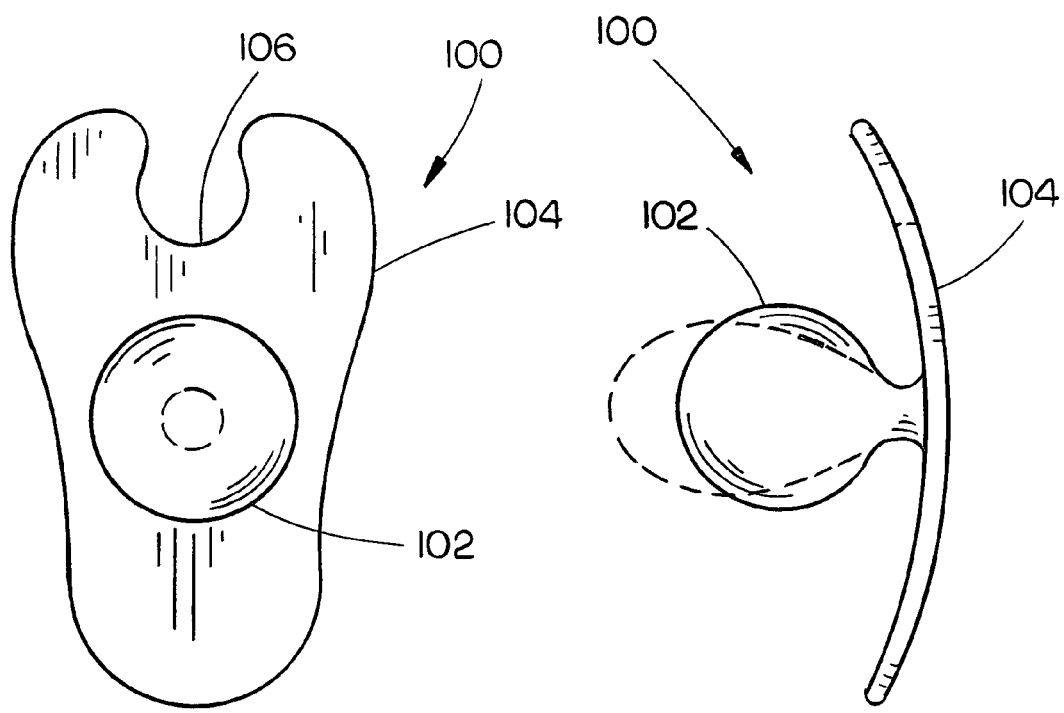
FIG. 2C is a top plan view of an alternative embodiment of the vaginal barrier and female urethral catheterization assisting device system.
FIG. 2D is a side-view of an alternative embodiment of the vaginal barrier and female urethral catheterization assisting device system.
Figures 3A, 3B:
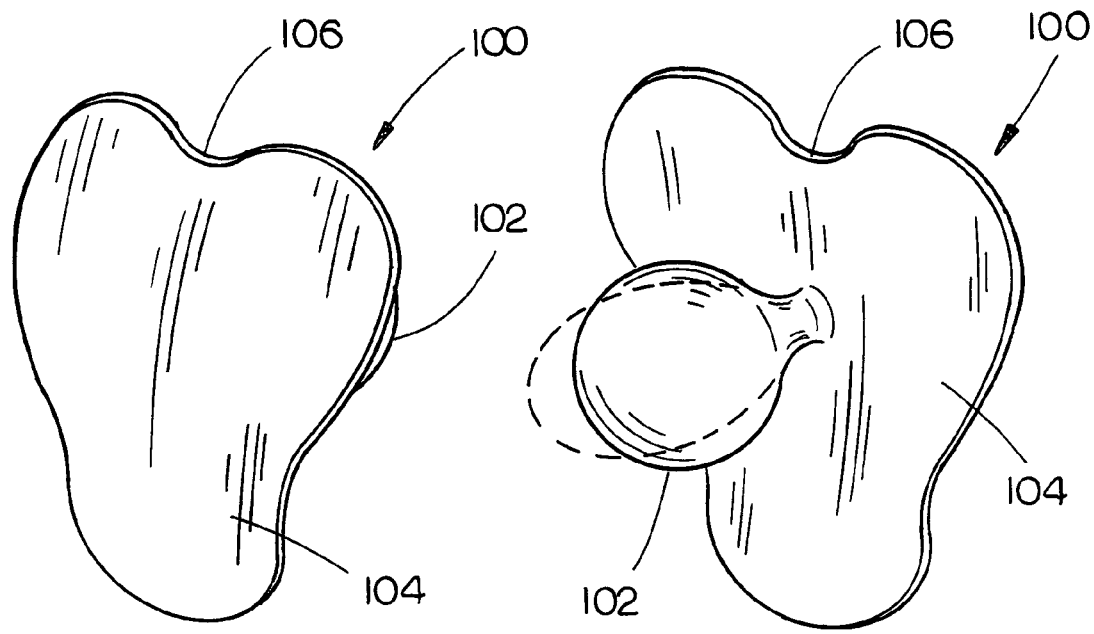
FIGS. 3A and 3B are isometric views of an alternative embodiment of the vaginal barrier and female urethral catheterization assisting device system.
Figures 3C, 3D:
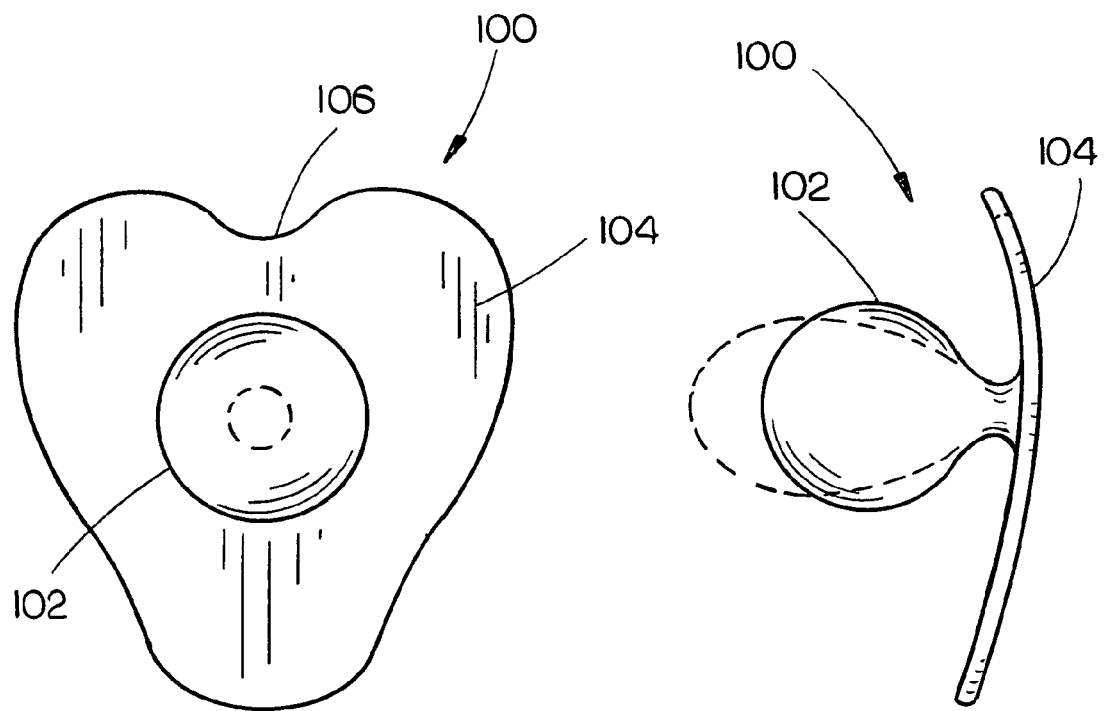
FIG. 3C is a top plan view of an alternative embodiment of the vaginal barrier and female urethral catheterization assisting device system.
FIG. 3D is a side-view of an alternative embodiment of the vaginal barrier and female urethral catheterization assisting device system.
Figure 4:
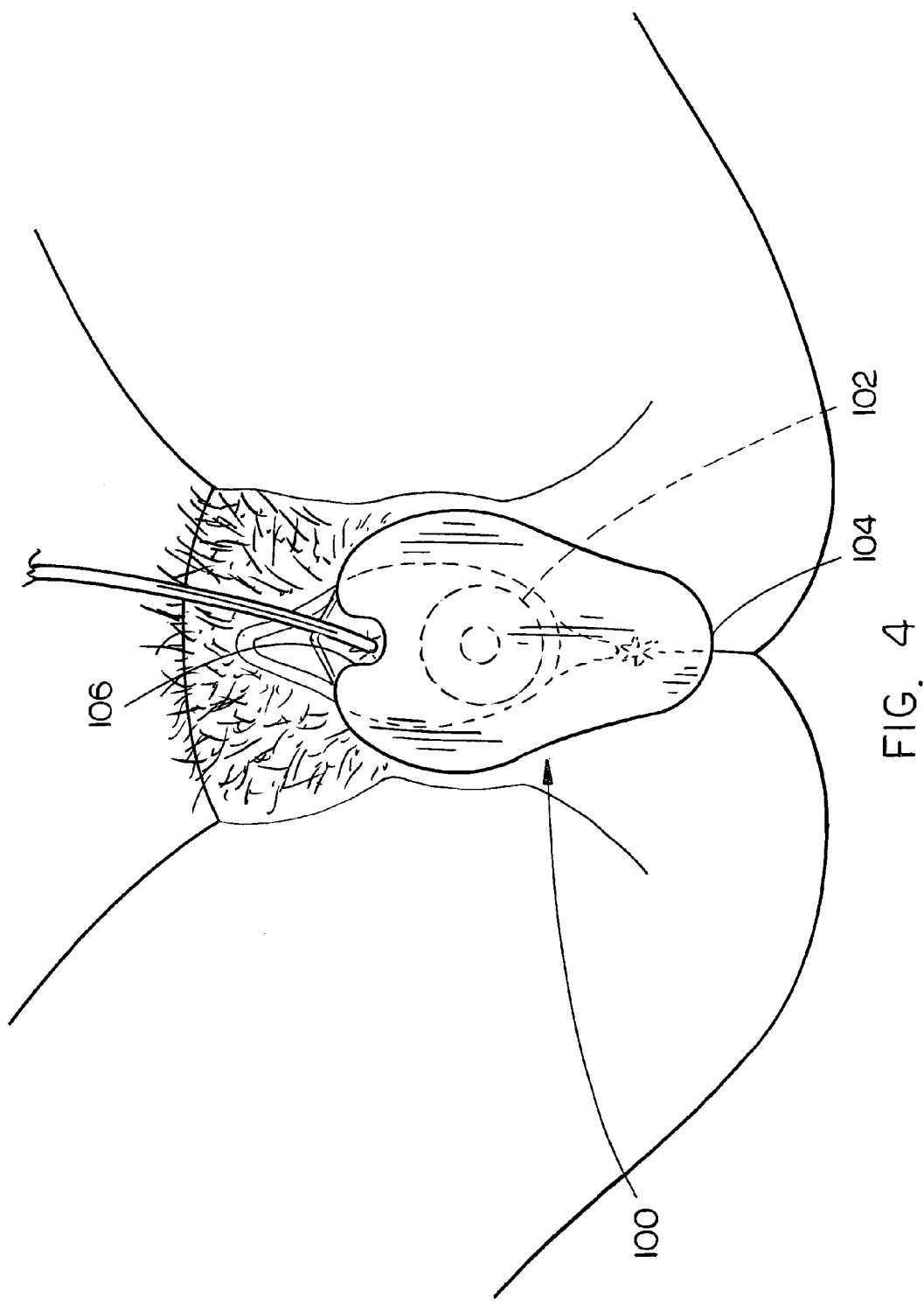
FIG. 4 is a partial view of the vaginal barrier and female urethral catheterization assisting device system illustrated in FIG. 1, applied to a patient.
Figure 5:
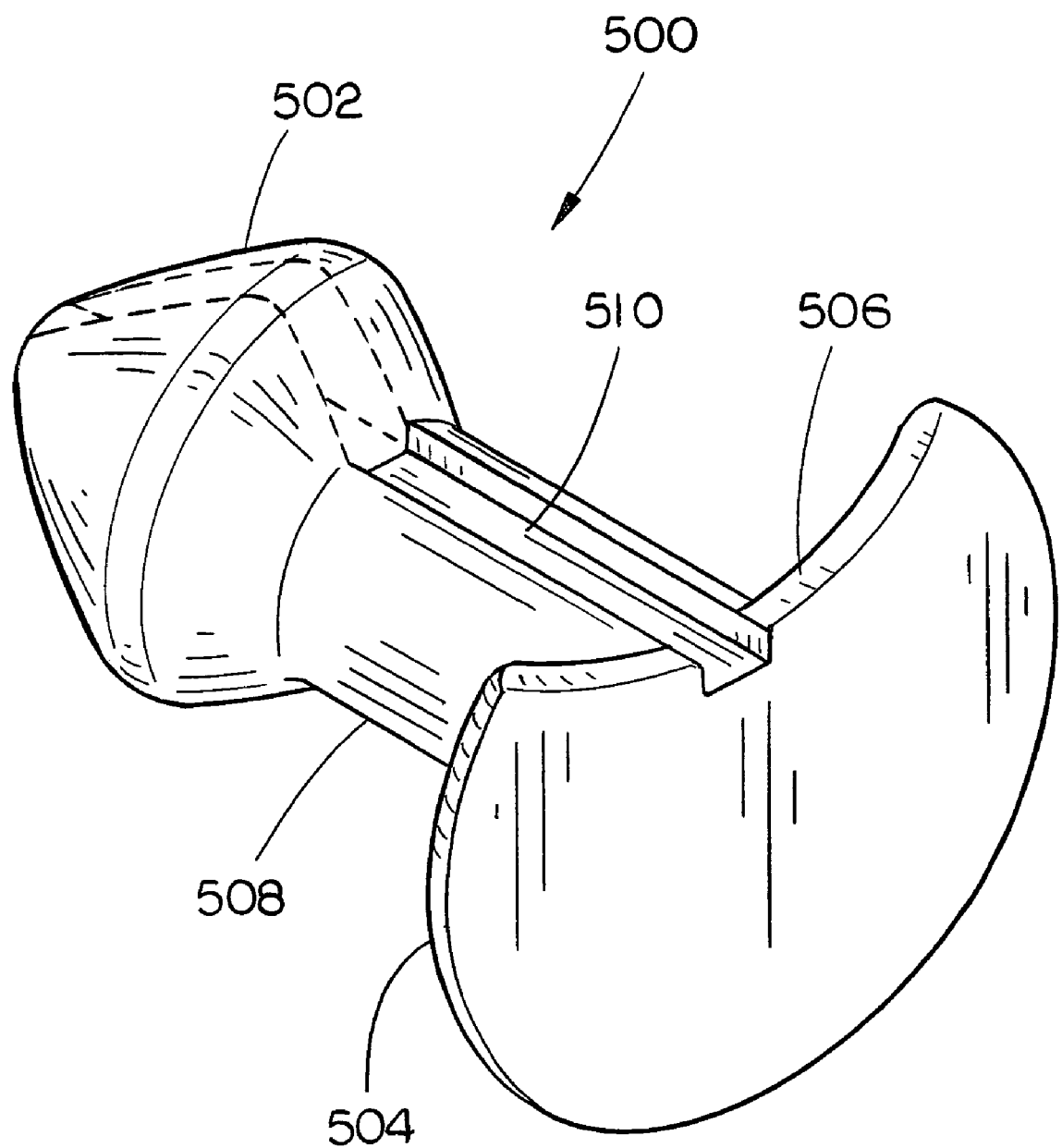
FIG. 5 is an isometric view of an alternative embodiment of the vaginal barrier and female urethral catheterization assisting device system.

Referring to FIG. 5, an alternative embodiment of a vaginal barrier and female urethral catheterization assisting device system 500 is illustrated. The system 500 may include a semi-rigid member 502 that is configured for positioning within a patient's vagina. The system 500 may include a generally longitudinal base member 504. The generally longitudinal base member 504 may define a recessed portion 506 distal to the semi-rigid member 502. The system 500 may also include a connector member 508. The connector member 508 may be disposed between the semi-rigid member 502 and the generally longitudinal base member 504. The recessed portion 506 may be configured to allow a catheter to be inserted into a urethra of the patient.

Connector member 508 may define a recessed channel 510. The recessed channel 510 may be defined at least partially between the semi-rigid member 502 and the generally longitudinal base member 504. In one embodiment, the recessed channel 510 may be defined by the connector member 508 longitudinally between the generally longitudinal base member 504 and the semi-rigid member 502, and continue to be defined by the semi-rigid member 502 at least partially from the portion distal the connector member 508 to an end opposite the connector member 508. For instance, the recessed channel 510 may reduce compression against a patient's urethra when the system 500 is properly inserted into the patient's vagina. The reduced compression may allow for easier insertion of a catheter into the patient's urethra.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed is:

1. A vaginal barrier and female urethral catheterization assisting device, comprising:
a vaginal positioning member configured for positioning within a vagina; and
a generally longitudinal base member, said generally longitudinal base member having a distal end and a proximal end, the generally longitudinal base member affixed to the vaginal positioning member, the generally longitudinal base member defining a partially open recessed portion, the partially open recessed portion having an opening, the opening of the partially open recessed portion being located at the distal end of the generally longitudinal base member, the vaginal positioning member being located between the distal end and the proximal end of the base member, the partially open recessed portion extending from the distal end of the base member toward the vaginal positioning member, the partially open recessed portion separating the distal end of the base member into a first lobe and a second lobe, the generally longitudinal base member being configured to form a barrier covering at least an area between the vagina and urethra of a patient, the proximal end of the generally longitudinal base member being configured to form a barrier covering an anus of a patient, the distal end of the base member being configured to separate a labia minora of a patient, wherein:
the partially open recessed portion is configured for allowing a catheter to be inserted into a urethra; and
the vaginal positioning member is configured to separate and at least partially interpose between the labia minora of the patient.

2. The device of claim 1, wherein at least one of the vaginal positioning member or the generally longitudinal base member is manufactured of silicone.

3. The device of claim 1, wherein at least one of the vaginal positioning member or the generally longitudinal base member is manufactured of plastic deposit.

4. The device of claim 1, wherein the vaginal positioning member is configured to reduce a vaginal prolapse of a patient.

5. A vaginal barrier and female urethral catheterization assisting device, comprising:
a vaginal positioning member configured for positioning within a vagina;
a generally longitudinal base member, said generally longitudinal base member having a distal end and a proximal end, the generally longitudinal base member affixed to the vaginal positioning member, the generally longitudinal base member defining a partially open recessed portion, the partially open recessed portion having an opening, the opening of the partially open recessed portion being located at the distal end of the generally longitudinal base member, the vaginal positioning member being located between the distal end and the proximal end of the base member, the partially open recessed portion extending from the distal end of the base member toward the vaginal positioning member, the partially open recessed portion separating the distal end of the base member into a first lobe and a second lobe, the generally longitudinal base member being configured to form a barrier covering at least an area between the vagina and urethra of a patient, the proximal end of the generally longitudinal base member being configured to form a barrier covering an anus of a patient, the distal end of the base member being configured to separate a labia minora of a patient;
a connector member, the connector member disposed between the vaginal positioning member and the generally longitudinal base member,
wherein:
the partially open recessed portion is configured for allowing a catheter to be inserted into a urethra; and
the connector member is configured to separate and at least partially interpose between the labia minora of the patient.

6. The device of claim 5, wherein at least one of the vaginal positioning member or the generally longitudinal base member is manufactured of silicone.

7. The device of claim 5, wherein at least one of the vaginal positioning member or the generally longitudinal base member is manufactured of plastic deposit.

8. The device of claim 5, wherein the connector member defines a recessed channel, the recessed channel at least partially disposed between the vaginal positioning member and the generally longitudinal base member, such recessed channel configured to reduce compression of the urethra.

9. The device of claim 5, wherein the vaginal positioning member is configured to reduce a vaginal prolapse of a patient.

* * * * *